United States Patent
Kang et al.

(10) Patent No.: US 11,696,727 B2
(45) Date of Patent: Jul. 11, 2023

(54) FOLDABLE ELECTRONIC DEVICE AND METHOD OF ESTIMATING BIO-INFORMATION USING THE SAME

(71) Applicant: SAMSUNG ELECTRONICS CO., LTD., Suwon-si (KR)

(72) Inventors: Jae Min Kang, Seoul (KR); Seung Woo Noh, Seongnam-si (KR); Sang Yun Park, Hwaseong-si (KR); Jin Woo Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 302 days.

(21) Appl. No.: 16/950,178

(22) Filed: Nov. 17, 2020

(65) Prior Publication Data

US 2021/0386375 A1    Dec. 16, 2021

(30) Foreign Application Priority Data

Jun. 15, 2020    (KR) .................. 10-2020-0072334

(51) Int. Cl.
*A61B 5/00*    (2006.01)
*A61B 5/022*    (2006.01)
(Continued)

(52) U.S. Cl.
CPC ........ *A61B 5/6843* (2013.01); *A61B 5/02116* (2013.01); *A61B 5/02225* (2013.01);
(Continued)

(58) Field of Classification Search
None
See application file for complete search history.

(56) References Cited

U.S. PATENT DOCUMENTS 9,742,456 B2    8/2017  Park et al.
2003/0093001 A1    5/2003  Martikainen
(Continued)

FOREIGN PATENT DOCUMENTS

KR    10-0660349 B1    12/2006
KR    10-2015-0023120 A    3/2015
(Continued)

OTHER PUBLICATIONS

Nam et. al., "Measurement of spatial pulse wave velocity by using a clip-type pulsimeter equipped with a Hall sensor and photoplethysmography", Sensors 2013, 13, 4714-4723. (Year: 2013).*
(Continued)

*Primary Examiner* — Yi-Shan Yang
(74) *Attorney, Agent, or Firm* — Sughrue Mion, PLLC

(57) ABSTRACT

The present disclosure relates to technology for estimating bio-information by using a foldable electronic device. The foldable electronic device includes a main body part, having a first main body and a second main body, configured to fold along a folding line; a first sensor provided on the first main body, and configured to obtain a contact image of an object of a user; a second sensor provided on the first main body, and configured to measure a degree of folding of the main body part; and a processor configured to estimate bio-information of the user, based on the contact image of the object and the degree of folding.

17 Claims, 15 Drawing Sheets

(51) Int. Cl.
*A61B 5/16* (2006.01)
*A61B 5/021* (2006.01)

(52) U.S. Cl.
CPC .......... *A61B 5/02241* (2013.01); *A61B 5/165* (2013.01); *A61B 5/6826* (2013.01); *A61B 5/7445* (2013.01)

(56) References Cited

U.S. PATENT DOCUMENTS

| | | | |
|---|---|---|---|
| 2015/0062078 A1* | 3/2015 | Christman | A61B 5/6897 345/174 |
| 2015/0182160 A1 | 7/2015 | Kim et al. | |
| 2017/0238825 A9 | 8/2017 | Fitzsimons et al. | |
| 2018/0200128 A1 | 7/2018 | Chun | |
| 2019/0110758 A1 | 4/2019 | Kang et al. | |
| 2019/0125187 A1 | 5/2019 | Kuo et al. | |
| 2020/0019745 A1 | 1/2020 | Kang et al. | |

FOREIGN PATENT DOCUMENTS

| | | |
|---|---|---|
| KR | 10-2015-0057185 A | 5/2015 |
| KR | 10-2015-0077684 A | 7/2015 |
| KR | 10-2019-0043464 A | 4/2019 |
| KR | 10-2020-0007312 A | 1/2020 |

OTHER PUBLICATIONS

Z. Gingl et al., "Universal Arduino-based experimenting systems to support teaching of natural sciences", Jan. 2019, pp. 1-9 (9pages total).

Dong-Hyun Nam et al., "Measurement of Spatial Pulse Wave Velocity by Using a Clip-Type Pulsimeter Equipped with a Hall Sensor and Photoplethysmography", Sensors, Apr. 9, 2013, vol. 13, pp. 4714-4723 (10 pages total).

Myung-Cheon Ahn et al., "Estimated Blood Pressure Algorithm of Wrist Wearable Pulsimeter Using by Hall Device", Journal of the Korean Magnetics Society, Jun. 2010, vol. 20, No. 3, pp. 106-113 (8 pages total).

Dae-Hui Lee et al., "Development of Oriental-Western Fusion Patient Monitor by Using the Clip-type Pulsimeter Equipped with a Hall Sensor, the Electrocardiograph, and the Photoplethysmograph", Journal of the Korean Magnetics Society, Aug. 20, 2013, vol. 23, No. 4, pp. 135-143 (9 pages total).

* cited by examiner

FOLDABLE ELECTRONIC DEVICE AND METHOD OF ESTIMATING BIO-INFORMATION USING THE SAME

CROSS-REFERENCE TO RELATED APPLICATION(S)

This application is based on and claims priority under 35 U.S.C. § 119 to Korean Patent Application No. 10-2020-0072334, filed on Jun. 15, 2020, in the Korean Intellectual Property Office, the disclosure of which is incorporated by reference herein in its entirety.

BACKGROUND

1. Field

The following description relates to a foldable electronic device, and technology for estimating bio-information by using the same.

2. Description of Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of the cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, a foldable electronic device may include a main body part, having a first main body and a second main body, configured to fold along a folding line; a first sensor provided on the first main body, and configured to obtain a contact image of an object of a user; a second sensor provided on the first main body, and configured to measure a degree of folding of the main body part; and a processor configured to estimate bio-information of the user, based on the contact image of the object and the degree of folding.

The first sensor may include an image sensor configured to obtain the contact image of the object based on the second main body rotating to press the object while the object is in contact with the first sensor.

The image sensor may include a complementary metal-oxide semiconductor (CMOS) image sensor (CIS).

The second sensor may include a Hall sensor configured to measure the degree of folding of the main body part based on the second main body rotating to press the object while the object contacts the first sensor.

The foldable electronic device may include a display part having a first display provided on an inner surface of the first main body, and a second display provided on an inner surface of the second main body.

The first display and the second display may be integrally formed with each other, and the display part may be configured to fold along the folding line.

The processor may control the display part to output a processing result.

The processor may control the first display to display a bio-information estimation result, and may control the second display to output information for estimating the bio-information.

The processor may control the second display to display a bio-information estimation history, and based on a user selecting an estimation history of a specific time, may control the first display to display a bio-information estimation result of the specific time.

The display part may include a third display provided on an outer surface of the second main body, and the processor may the third display to display information for guiding contact pressure between the object and the first sensor based on the degree of folding measured by the second sensor.

The processor may obtain a pulse wave signal based on the contact image, and obtain contact pressure, exerted by the second main body on the object, based on the degree of folding.

The processor may obtain an oscillometric waveform envelope based on the pulse wave signal and the contact pressure, and estimate bio-information based on the obtained oscillometric waveform envelope.

The bio-information may include one or more of blood pressure, vascular age, arterial stiffness, aortic pressure waveform, vascular compliance, stress index, and fatigue level.

According to an aspect of an example embodiment, a method of estimating bio-information of a user, by a foldable electronic device comprising a foldable main body part having a first main body and a second main body, may include obtaining a contact image of an object of the user by a first sensor provided on the first main body; measuring a degree of folding of the main body part by a second sensor provided on the first main body; and estimating the bio-information of the user, based on the contact image and the degree of folding.

The obtaining the contact image may include obtaining the contact image of the object based on the second main body rotating to press the object while the object contacts the first sensor.

The measuring the degree of folding may include measuring the degree of folding of the main body part based on the second main body rotating to press the object while the object contacts the first sensor.

The estimating the bio-information may include obtaining a pulse wave signal based on the contact image; obtaining contact pressure, exerted by the second main body on the object when the second main body rotates, based on the degree of folding; and estimating the bio-information of the user, based on the pulse wave signal and the contact pressure.

The estimating the bio-information may include obtaining an oscillometric waveform envelope based on the pulse wave signal and the contact pressure; and estimating the bio-information based on the obtained oscillometric waveform envelope.

The method may include outputting information for guiding contact pressure between the object and the first sensor based on the measured degree of folding, on a display provided on an outer surface of the second main body.

The method may include outputting an estimation result of the bio-information.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1A:
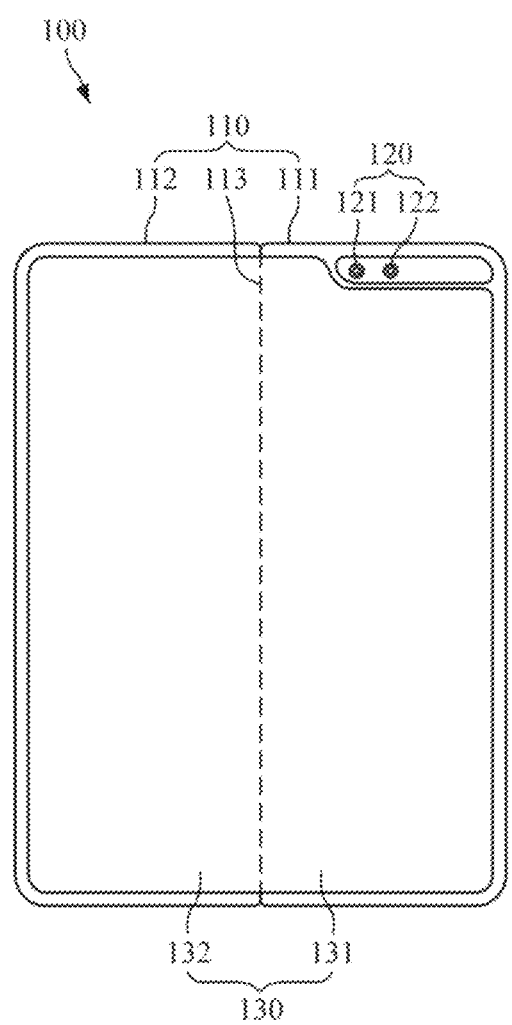
FIGS. 1A to 1C are diagrams illustrating examples of a foldable electronic device.

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, and may further include one or more other elements, unless explicitly described to the contrary. In the following description, terms such as "unit" and "module" indicate a unit for processing at least one function or operation and units may be implemented by using hardware, software, or a combination thereof.

Hereinafter, embodiments of a foldable electronic device and a method of estimating bio-information using the same will be described in detail with reference to the accompanying drawings.

Figure 1B:
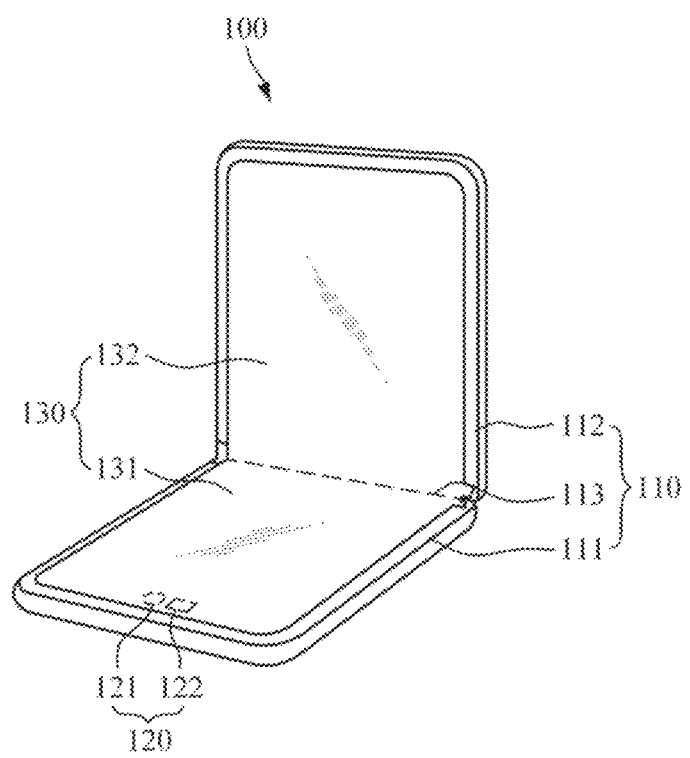
Figure 1C:
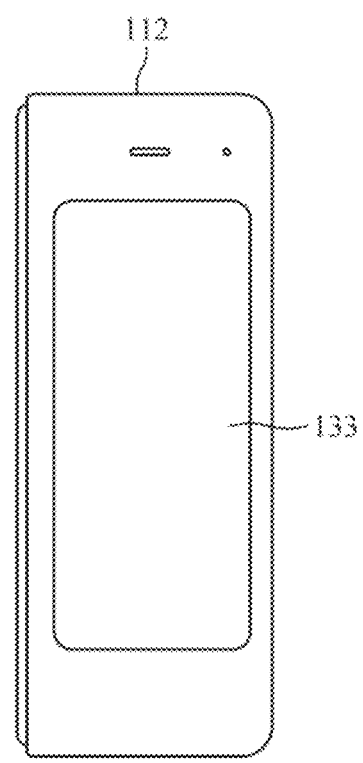

FIGS. 1A to 1C are diagrams illustrating examples of a foldable electronic device.

FIG. 1A is a diagram illustrating a vertical-type foldable electronic device 100, and FIG. 1B is a diagram illustrating a horizontal-type foldable electronic device 100. Referring to FIGS. 1A and 1B, embodiments of the foldable electronic device 100 may include a main body part 110, a sensor part 120 disposed at the main body part 110, and a display part 130 disposed at the main body part 110.

The main body part 110 includes a first main body 111 and a second main body 112, which are disposed along a folding line 113, and may be connected to each other via a hinge. Further, the first main body 111 and the second main body 112 may be folded and unfolded by rotating with respect to the folding line 113. In this case, while the first main body 111 and the second main body 112 rotate, a display surface thereof may be folded inward. The display surface of the main body part 110 refers to a surface on which a first display 131 and a second display 132 of the display part 130 are disposed. However, the display surface is not limited thereto and may be folded in an opposite direction.

As illustrated herein, the sensor part 120 may be disposed in a predetermined area of the first main body 111. The sensor part 120 may include a first sensor 121 and a second sensor 122. The first sensor 121 may obtain a contact image of an object when the object is in contact with the sensor. In this case, the object may be a user's finger, and the contact image of the object may be a fingerprint image of the finger.

The first sensor 121 may be an optical image sensor, such as a complementary metal-oxide semiconductor (CMOS) image sensor (CIS), but is not limited thereto. The first sensor 121 may include a light source for emitting light onto the object in contact with the first sensor 121. The light source may include a light emitting diode (LED), a laser diode, and the like, and may be formed as one or more arrays of a plurality of light sources. However, the light source is not limited thereto, and the first sensor 121 may use, for example, light emanating from the first display 131 and/or the second display 132 of the display part 130 as an external light source.

Further, the first sensor 121 may include a pixel array, and each pixel of the pixel array may include a detector such as a photo diode, a photo transistor, and the like. A detector of each pixel may detect light scattered or reflected from the object, and may output pixel data representing a contact image of the object.

The second sensor 122 may measure a degree of folding when the first main body 111 and the second main body 112 are folded by rotating. For example, the second sensor 122 may include a Hall sensor, which outputs a value indicative of a degree of folding of the main body part 110 by using the Hall effect occurring when the second main body 112 rotates. However, the second sensor 122 is not limited thereto.

Although not illustrated herein, the sensor part 120 may further include one or more additional image sensors in the first main body 111 and/or the second main body 112. For example, an additional image sensor may perform various functions, including a function of guiding a contact position of the object by photographing the object while the first sensor 121 acquires a contact image of the object.

The display part 130 includes the first display 131 and the second display 132, which may be disposed on a display surface of the first main body 111 and the second main body 112, respectively. The first display 131 and the second display 132 may be integrally formed with each other, and may be made of a flexible material so that the first display 131 and the second display 132 may be folded and unfolded when the first main body 111 and the second main body 112 rotate along the folding line 113. However, the first display 131 and the second display 132 are not limited thereto, and may be separated from each other to be disposed at the first main body 111 and the second main body 112, respectively. The first display 131 and the second display 132 may include a touch screen for receiving a touch input. Further, the first display 131 and the second display 132 may also include a fingerprint sensor for acquiring a fingerprint image when a user's body part touches the sensor.

Referring to FIG. 1C, the display part 130 may further include a third display 133 disposed on one surface of the main body part 110 (hereinafter referred to as a "cover surface"), which is exposed to the outside when the main body part 110 is folded. For example, the third display 133 may be disposed on a cover surface of the second main body 112 as illustrated in FIG. 1C. The third display 133 may also include a touch screen for receiving a touch input and/or a fingerprint sensor for acquiring a fingerprint image of a finger. However, the third display 133 may be omitted. For convenience of explanation, FIG. 1C illustrates an example in which the third display 133 is disposed on a cover surface of the vertical-type foldable electronic device 100, but the same also applies to the horizontal-type foldable electronic device 100.

While the main body part 110 is folded, a user may input instructions, such as a request for estimating bio-information, a request for displaying bio-information estimation history, and a request for outputting a health monitoring result, through the third display 133. Furthermore, when a user unfolds the third display 133 during an operation for estimating bio-information through the third display 133, information displayed on the third display 133 may be enlarged on the first display 131 and the second display 132.

The foldable electronic device 100 may include a processor for processing various functions thereof, and various other hardware modules, such as a communication module, a storage module, and the like, which are mounted in the main body part 110. For example, the processor may control the sensor part 120 in response to a request for estimating bio-information, and may estimate bio-information based on the contact image of the object, obtained by the first sensor 121, and a degree of folding of the main body part 110, output by the second sensor 122. In this case, bio-information may include, but is not limited to, blood pressure, vascular age, arterial stiffness, aortic pressure waveform, vascular compliance, stress index, fatigue level, skin elasticity, skin age, and the like.

Figure 2:
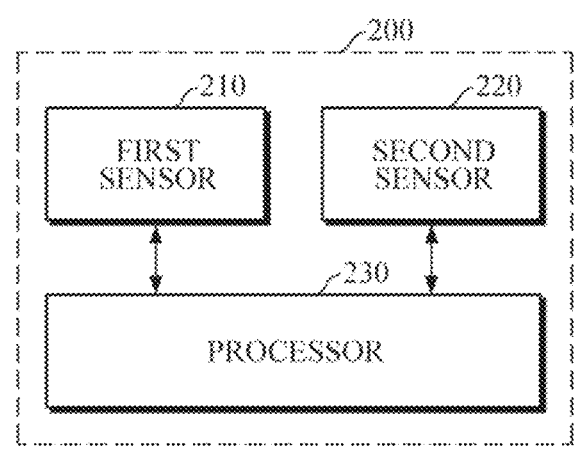
FIG. 2 is a block diagram illustrating a foldable electronic device according to an embodiment of the present disclosure.

FIG. 2 is a block diagram illustrating a foldable electronic device according to an embodiment of the present disclosure. FIGS. 3A to 3E are diagrams explaining examples of estimating bio-information.

Referring to FIG. 2, the foldable electronic device 200 according to an embodiment includes a first sensor 210, a second sensor 220, and a processor 230.

Based on receiving a request for estimating bio-information, the processor 230 may control the first sensor 210 and the second sensor 220, and may estimate bio-information based on a contact image and a degree of folding, which are obtained by the first sensor 210 and the second sensor 220, respectively.

Figure 3A:
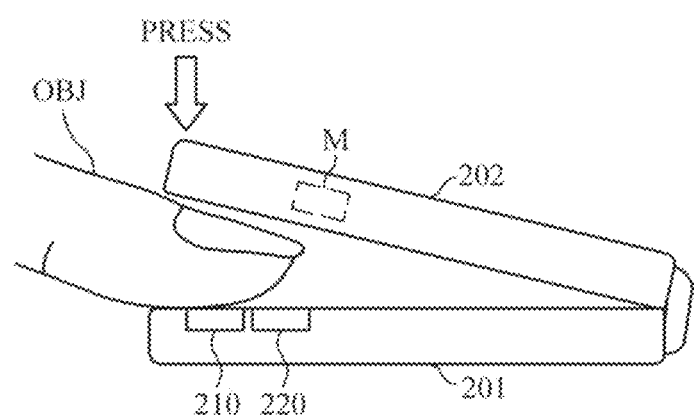
FIGS. 3A to 3E are diagrams explaining examples of estimating bio-information.

Referring to FIG. 3A, when a user places a finger OBJ on the first sensor 210 and gradually increases or decreases a pressing force on the finger by rotating a second main body 202, the first sensor 210 may obtain the contact image of the finger OBJ for a predetermined period of time.

Figure 3B:
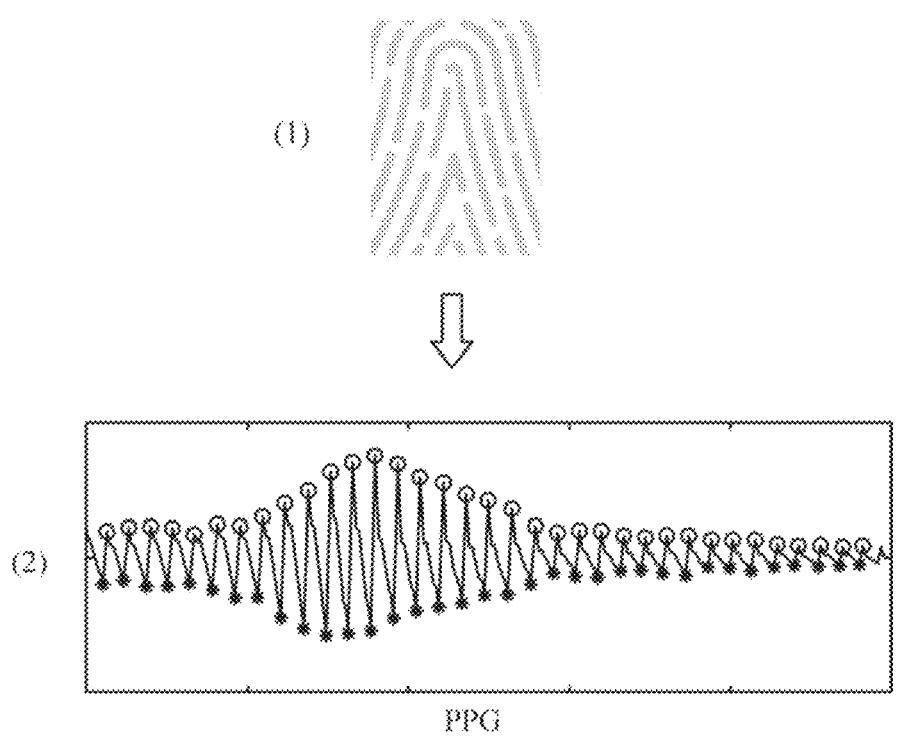

The processor 230 may obtain a pulse wave signal based on a change in pixel intensity of the contact image received from the first sensor 210. Referring to FIG. 3B, (1) shows the contact image of the object which is acquired by the first sensor 210. Based on receiving pixel data representative of contact images which are acquired successively during a predetermined period of time, the processor 230 may obtain a pulse wave signal, as shown in (2), based on the change in pixel intensity of the received pixel data.

For example, the processor 230 may convert the pixel intensity at each time point of the predetermined period of time into a pulse wave amplitude at each time point by using an amplitude conversion model which represents a correlation between the pixel intensity and the amplitude. For example, the amplitude conversion model may be an equation for calculating an average of the pixel intensities, but is not limited thereto. In addition, the processor 230 may set a region of interest by using the contact image, and may obtain an amplitude based on the intensity of pixels in the set region of interest. In this case, the processor 230 may set the region of interest based on a predetermined characteristic point, such as a center point of a fingerprint or a center point of the contact image.

Referring back to FIG. 3A, based on the Hall effect produced by a magnet M, embedded in the second main body 202, when the second main body 112 rotates, the second sensor 220 may output a value indicating a degree of folding between the first main body 201 and the second main body 202.

Figure 3C:
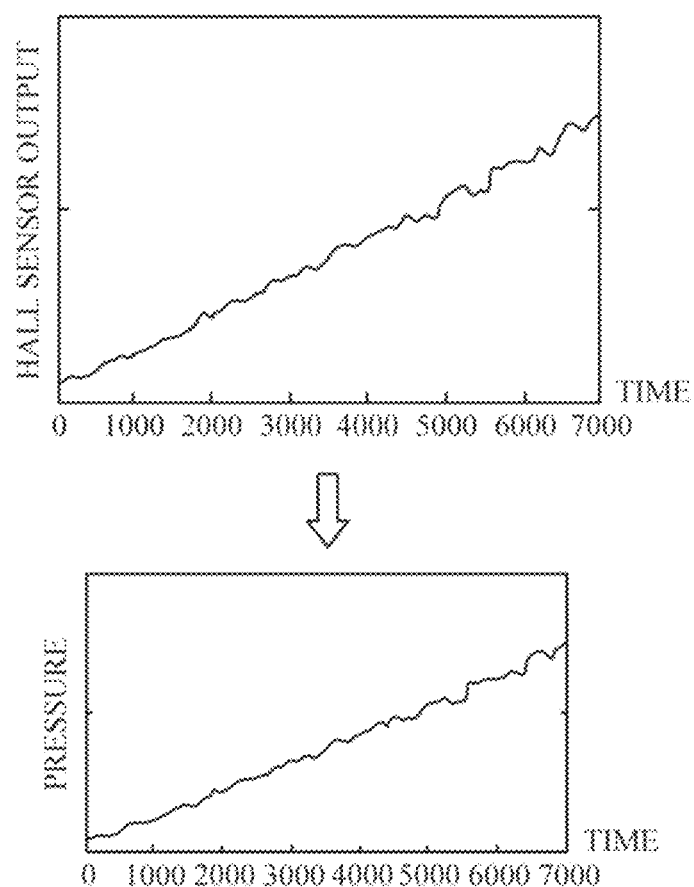

In FIG. 3C, (1) illustrates a signal output by the second sensor 220 when a user places a finger OBJ on the first sensor 210 and then gradually increases a pressing force on the finger by rotating the second main body 202. The processor 230 may convert values, indicating degrees of folding output by the second sensor 220, into contact pressure values as illustrated in (2) of FIG. 3. For example, by using a conversion model which defines a correlation between the output values of the second sensor 220 and contact pressure values, the processor 230 may convert the output values into contact pressure values.

Based on obtaining the pulse wave signal and the contact pressure, the processor 230 may estimate bio-information based on the obtained pulse wave signal and contact pressure. For example, the processor 230 may estimate blood pressure using oscillometry based on the pulse wave signal and the contact pressure.

Figure 3D:
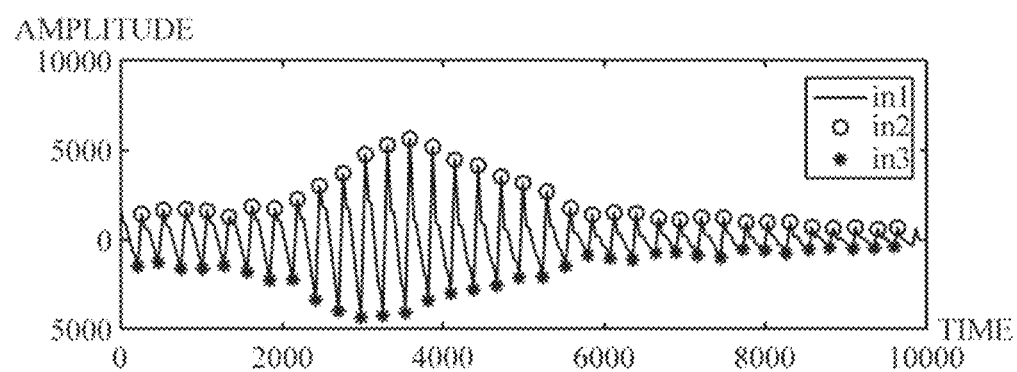
Figure 3E:
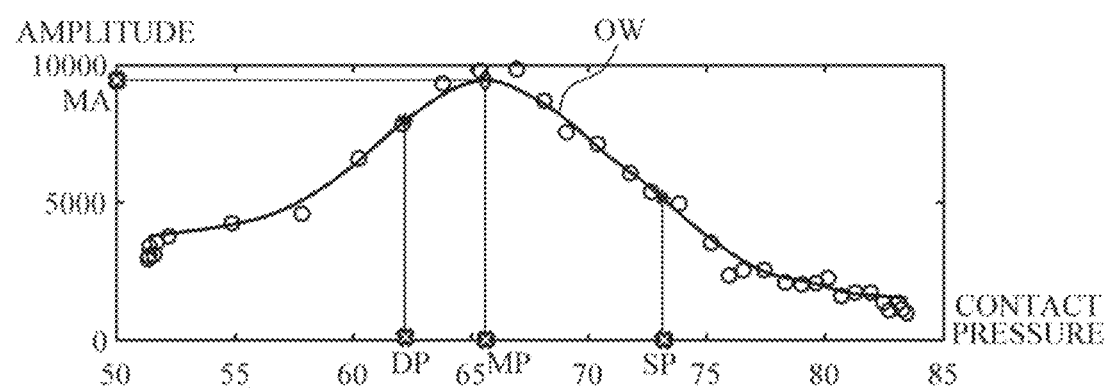

FIGS. 3D and 3E are diagrams illustrating an example of estimating blood pressure using oscillometry.

FIG. 3D is a diagram illustrating an example of a pulse wave signal obtained as described above. As illustrated in FIG. 3D, when a user places an object on the first sensor 210 and gradually increases a pressing force of the second main body 202 on the object, the amplitude of the pulse wave signal shows a gradually increasing trend during a predetermined period of time. The processor 230 may extract a peak-to-peak point of the pulse wave signal waveform by subtracting a negative (−) amplitude value in3 from a positive (+) amplitude value in2 of a waveform envelope in1 at each measurement time, and may obtain the oscillometric waveform envelope OW by plotting the peak-to-peak amplitude at each measurement time against the contact pressure value at the same point in time, as illustrated in FIG. 3E.

Referring to FIG. 3E, the processor 230 may obtain features from the obtained oscillometric waveform envelope OW. The processor 230 may obtain, as features, an amplitude value MA at a maximum peak point, a contact pressure value MP at the maximum peak point, contact pressure values SP and DP at the left and right points corresponding to amplitude values having a preset peak ratio (e.g., 0.5 to 0.7) to the amplitude value MA at the maximum peak point, and the like from the oscillometric waveform envelope OW. However, the features are not limited thereto, and the processor 230 may obtain additional features, such as a maximum amplitude value, a time value corresponding to the maximum amplitude value, time and amplitude values at points related to a propagation wave and a reflection wave, a combination of the obtained values, and the like.

Based on extracting the features, the processor 230 may estimate blood pressure by applying a pre-defined blood pressure estimation model. The blood pressure estimation model may be defined as various linear or non-linear combination functions, such as addition, subtraction, division, multiplication, logarithmic value, regression equation, and the like, with no specific limitation. For example, the following Equation 1 represents a simple linear function.

$$y=ax+b \qquad [\text{Equation 1}]$$

Herein, "y" denotes an estimated blood pressure value to be obtained; "x" denotes an extracted feature value; and "a" and "b" are values pre-obtained by preprocessing, and may be values personalized for each user. For example, by using the above Equation 1 which is defined for each of mean arterial pressure (MAP), diastolic blood pressure (DBP), and systolic blood pressure (SBP), the processor 230 may independently estimate each blood pressure. For example, by inputting the extracted feature values MP, DP, and SP into the function, which is defined for each of the feature values, the processor 230 may obtain MAP, DBP, and SBP independently.

Figure 4:
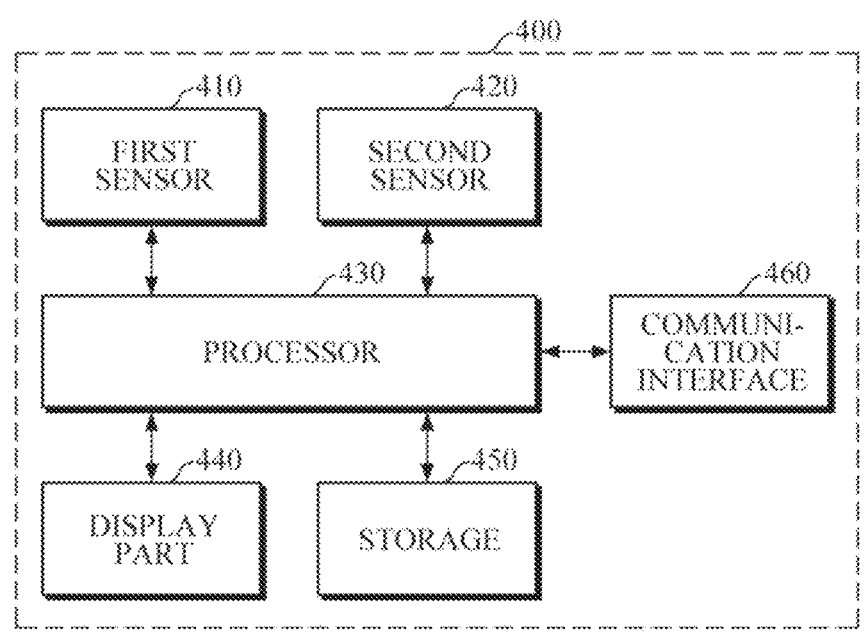
FIG. 4 is a block diagram illustrating a foldable electronic device according to another embodiment of the present disclosure.

FIG. 4 is a block diagram illustrating a foldable electronic device according to another embodiment of the present disclosure. FIGS. 5A to 5D are diagrams illustrating examples of outputting information on a display part.

As illustrated in FIG. 4, a foldable electronic device 400 includes a first sensor 410, a second sensor 420, a processor 430, a display part 440, a storage 450, and a communication interface 460. The first sensor 410, the second sensor 420, the processor 430, and the display part 440 are described above in detail, such that redundant description will be omitted.

Figure 5A:
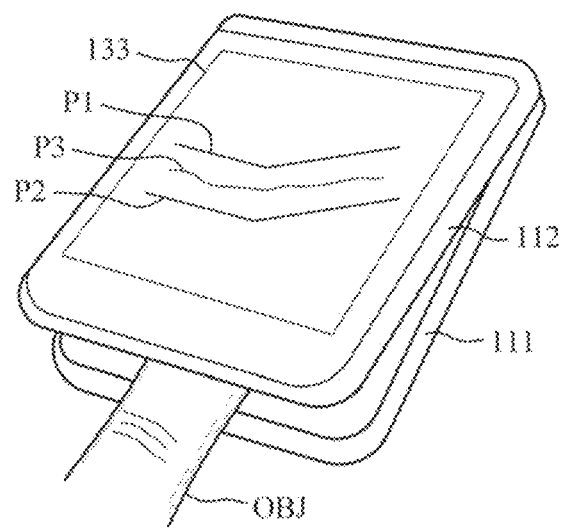
FIGS. 5A to 5D are diagrams illustrating examples of outputting information on a display part.

Referring to FIGS. 4 and 5A, based on receiving a request for estimating bio-information, the processor 430 may guide a user in measuring bio-information by providing information on a contact position, contact pressure, and the like, of the object OBJ.

For example, the processor 430 may output information, such as "place your finger on the first sensor," by voice using a speaker of the foldable electronic device 400.

In another example, when the main body is folded, the processor 430 may display a visual marker, indicating a contact position of the finger, on the third display 133 disposed on the cover surface of the second main body 112; and when the main body is unfolded, the processor 430 may display the visual marker on the first display or the second display disposed on the display surface of the first main body 111 and the second main body 112.

In yet another example, when the user places the object OBJ on the first sensor 410, the processor 430 may display voice or visual information, such as "fold the main body to press the finger," through a speaker or a display as guide information for the user. In this case, when the user rotates and folds the second main body 112, the guide information displayed on the first display or the second display may be moved to the third display 133 to be continuously displayed thereon.

In still another example, as illustrated in FIG. 5A, when the user places the finger on the first sensor 410, the processor 430 may display, on the third display 133, markers P1 and P2 for guiding reference contact pressures to be applied by the second main body 112 to the finger. Furthermore, when the user gradually increases a pressing force on the finger by rotating the second main body 112 according to guide information on the reference contact pressures P1 and P2, the processor 430 may obtain contact pressure based on a degree of folding measured by the second sensor 420, and may display a marker P3, indicating an actual contact pressure, on the third display 133 for the user.

Figure 5B:
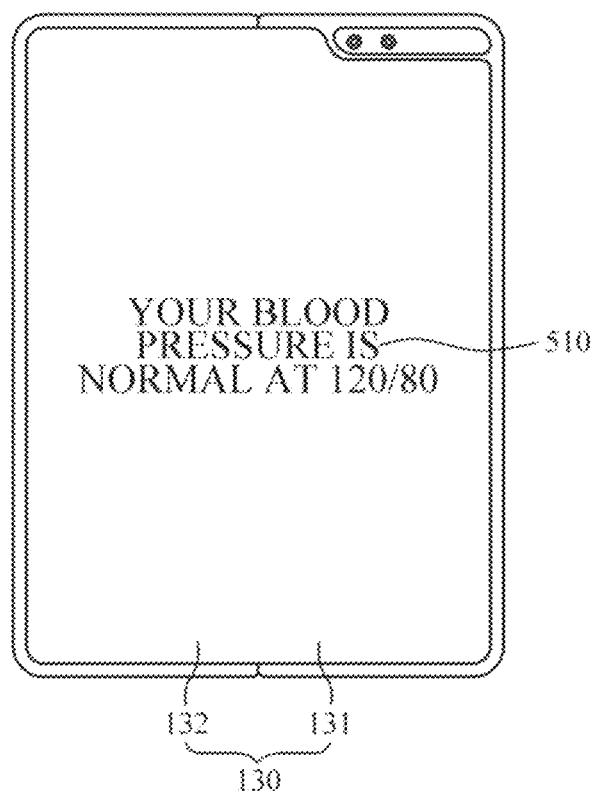
Figure 5C:
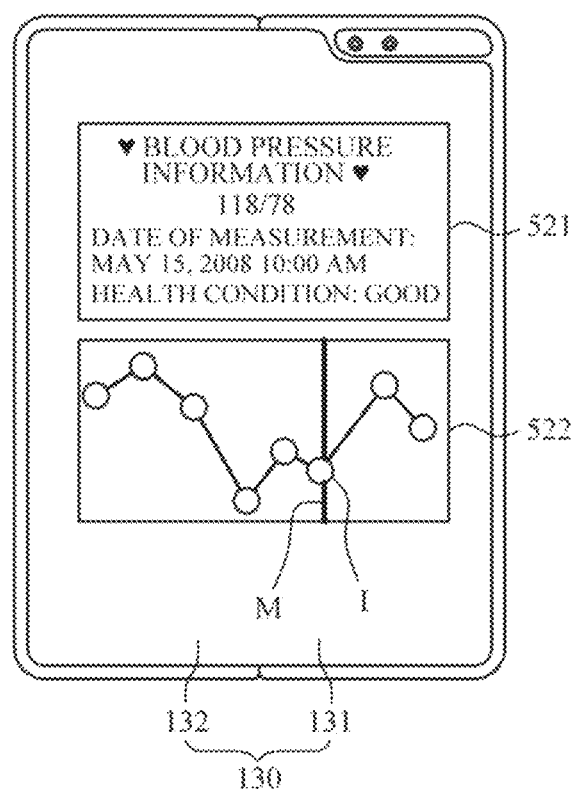

Referring to FIGS. 4, 5B and 5C, based on completing estimation of bio-information, the processor 430 may display a bio-information estimation result on the display part 440.

For example, as illustrated in FIG. 5B, when the main body is unfolded, the processor 430 may display an estimated blood pressure value and/or information on whether the estimated blood pressure value is normal at the center of the first display 131 and the second display 132 of the display part 440. In this case, when the user folds the main body, the processor 430 may move the estimated blood pressure value to the third display so that the blood pressure value may be displayed on the third display.

Figure 5D:
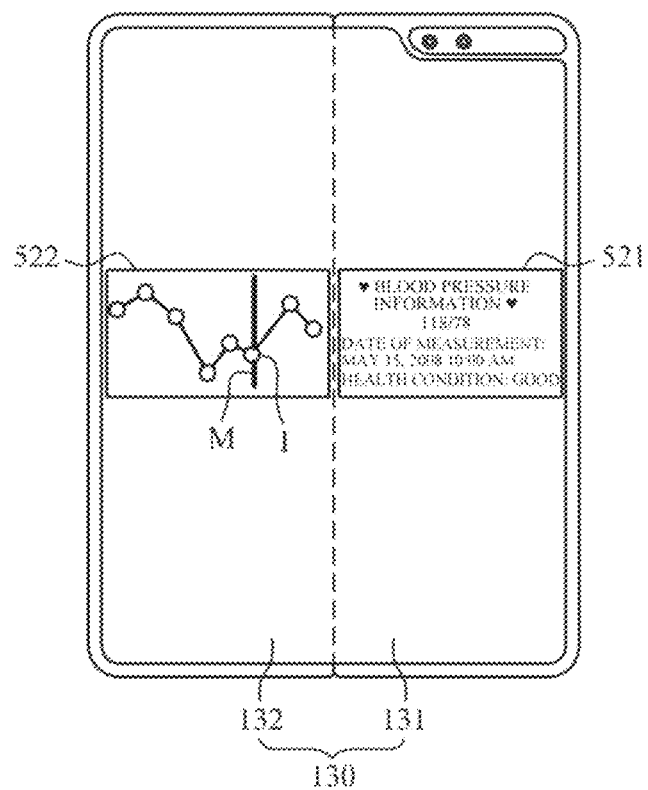

In another example, as illustrated in FIGS. 5C and 5D, when the main body is unfolded, the processor 430 may display, on the display part 440, a graph showing a blood pressure estimation history, blood pressure estimation history information 522 showing a first marker I indicating each estimation time, and a second marker M indicating a currently selected estimation time, and a blood pressure estimation result 521 at a selected time when the user selects a specific estimation time by moving the second marker I. In this case, the processor 430 may display the blood pressure estimation result 521 and the blood pressure estimation history information 522 on an upper end or a lower end of the first display 131 and the second display 132 as illustrated in FIG. 5C, or on the first display 131 and the second display 132 as illustrated in FIG. 5D.

The storage 450 may store a variety of information related to bio-information such as contact image data, a degree of folding between the first and second main bodies, a pulse wave signal, contact pressure, an estimated bio-information value, health condition monitoring information, and the like. Furthermore, the storage 450 may store reference information for estimating bio-information such as user characteristics information, such as a user's age, sex, stature, weight, health condition, and the like, a bio-information estimation model, an amplitude conversion model, and the like, but the reference information is not limited thereto.

In this case, the storage 450 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 460 may communicate with an external device by using wired or wireless communication techniques under the control of the processor 430, and may transmit and receive various data to and from the external device. For example, the communication interface 460 may transmit a bio-information estimation result to the external device, and may receive, from the external device, a variety of reference information for estimating bio-information. In this case, the external device may include a cuff-type blood pressure measuring device, and an information processing device such as a smartphone, a tablet personal computer (PC), a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, this is merely exemplary and is not intended to be limiting.

Figure 6:
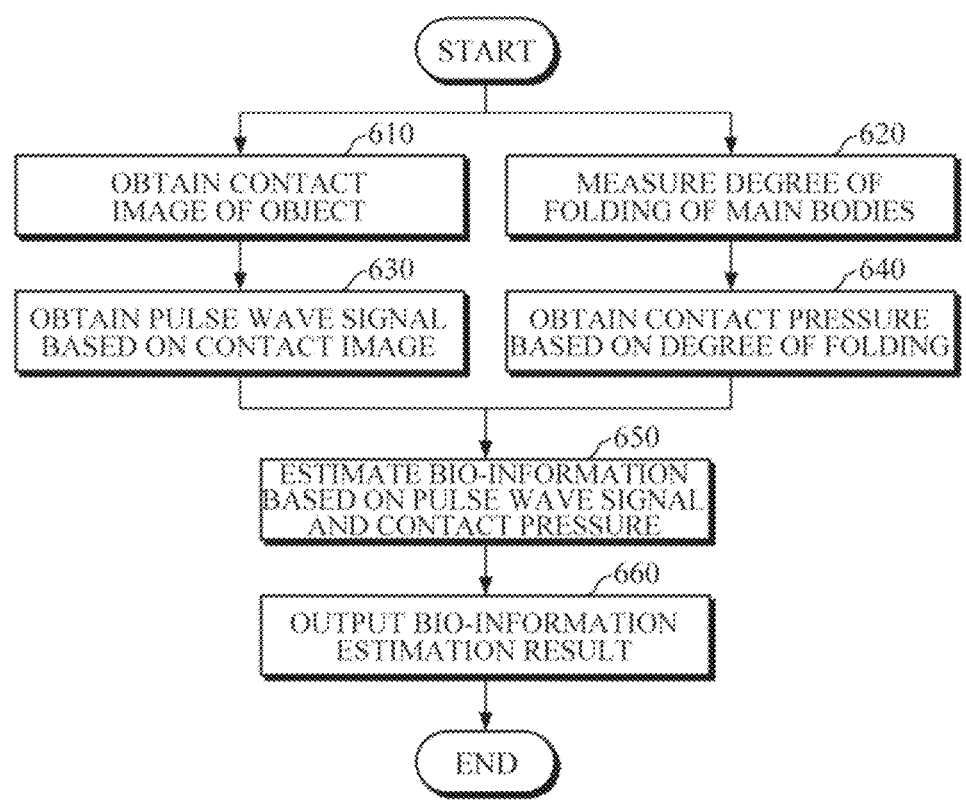
FIG. 6 is a flowchart illustrating a method of estimating bio-information according to an embodiment of the present disclosure.

FIG. 6 is a flowchart illustrating a method of estimating bio-information according to an embodiment of the present disclosure. The method of FIG. 6 is performed by the embodiments of the foldable electronic devices 200 and 400, which will be briefly described below in order to avoid redundancy.

The foldable electronic devices 200 and 400 may obtain a contact image of an object by using the first sensor disposed at the first main body of the main body part in operation 610. In this case, the first sensor may include a CIS, and may obtain a contact image of the object when a user places the object on the first sensor and then applies gradually increasing or decreasing pressure to the object by rotating the second main body.

The foldable electronic devices 200 and 400 may measure a degree of folding between the first main body and the second main body in operation 620 by using the second sensor while the user changes pressure, applied to the object, by rotating the second main body. In this case, the degree of folding may be an angle formed between the first main body and the second main body, and the second sensor may include a Hall sensor.

Then, the foldable electronic devices 200 and 400 may obtain a pulse wave signal in operation 630 based on the contact image obtained in operation 610. In this case, the foldable electronic devices 200 and 400 may extract a change in pulse wave amplitude based on a change in pixel intensity of the contact images of the object which are obtained successively during a predetermined period of time.

Subsequently, the foldable electronic devices 200 and 400 may obtain contact pressure in operation 640 based on the degree of folding of the main bodies which is measured in operation 620. By using a pre-defined contact pressure conversion model, the foldable electronic devices 200 and 400 may convert a change in the degree of folding during a predetermined period of time into a change in the contact pressure.

Next, the foldable electronic devices 200 and 400 may estimate bio-information based on the pulse wave signal and the contact pressure in operation 650. For example, based on a relationship between the amplitude of the pulse wave signal and the contact pressure, the foldable electronic devices 200 and 400 may estimate blood pressure using oscillometry.

Then, the foldable electronic devices 200 and 400 may output a bio-information estimation result in operation 660. The foldable electronic devices 200 and 400 may output the bio-information estimation result in various manners by using a plurality of displays disposed on a display surface of the first main body, a display surface of the second main body, a cover surface of the second main body, and the like.

Further, the foldable electronic devices 200 and 400 may provide a user with the bio-information estimation result, a health condition, and the like, by voice, vibrations, tactile sensation, and the like, by using a speaker, a haptic module, and the like.

The example embodiments of the present disclosure can be implemented by computer-readable code, written on a non-transitory computer-readable medium, that is executed by a processor. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium can be distributed over a plurality of computer systems connected to a network so that computer-readable code is written thereto and executed therefrom in a decentralized manner. Functional programs, code, and code segments for implementing the example embodiments of the present disclosure can be deduced by programmers in the technical field to which the present disclosure pertains.

The present disclosure has been described herein with regard to various example embodiments. However, it will be obvious to those skilled in the art that various changes and modifications can be made without changing the technical conception and features of the present disclosure. Thus, it is clear that the above-described embodiments are illustrative in all aspects and are not intended to limit the present disclosure.

What is claimed is:

1. A foldable electronic device, comprising:
   a main body part, having a first main body including a first display and a second main body including a second display, configured to fold along a folding line such that the first display and the second display face each other when the main body part is folded along the folding line;
   a first sensor provided on the first main body, and configured to obtain a contact image of an object of a user placed into contact with the first main body;
   a second sensor provided on the first main body, and configured to measure a degree of folding of the first main body relative to the second main body while the object is placed into contact with the first main body; and
   a processor configured to estimate bio-information of the user, based on a signal obtained from the contact image of the object and the degree of folding,
   wherein the obtained signal provides bio-information corresponding to one or more of blood pressure, vascular age, arterial stiffness, aortic pressure waveform, vascular compliance, stress index, and fatigue level of the user.

2. The foldable electronic device of claim 1, wherein the first sensor comprises an image sensor configured to obtain the contact image of the object when the second main body is rotated to press the object against the first main body while the object is in contact with the first sensor on the first main body.

3. The foldable electronic device of claim 2, wherein the image sensor comprises a complementary metal-oxide semiconductor (CMOS) image sensor (CIS).

4. The foldable electronic device of claim 1, wherein the second sensor comprises a Hall sensor configured to measure the degree of folding of the main body part based on the second main body rotating to press the object while the object contacts the first sensor.

5. The foldable electronic device of claim 1, wherein the first display and the second display are integrally formed with each other to form a display part, and the display part is configured to fold along the folding line.

6. The foldable electronic device of claim 1, wherein the first display and the second display are integrally formed with each other to form a display part, and the processor is further configured to control the display part to output a processing result.

7. The foldable electronic device of claim 6, wherein the processor is further configured to control the first display to display a bio-information estimation result, and is further configured to control the second display to output information for estimating the bio-information.

8. The foldable electronic device of claim 7, wherein the processor is further configured to control the second display to display a bio-information estimation history, and based on a user selecting an estimation history of a specific time, is further configured to control the first display to display a bio-information estimation result of the specific time.

9. The foldable electronic device of claim 1, further comprising a third display provided on an outer surface of the second main body, and
wherein the processor is further configured to control the third display to display information for guiding the user to provide contact pressure against the object and first main body having the first sensor based on the degree of folding measured by the second sensor.

10. The foldable electronic device of claim 1, wherein the processor is further configured to obtain a pulse wave signal as the signal based on the contact image, and obtain contact pressure, exerted by the second main body on the object, based on the degree of folding.

11. The foldable electronic device of claim 10, wherein the processor is further configured to obtain an oscillometric waveform envelope based on the pulse wave signal and the contact pressure, and estimate the bio-information based on the obtained oscillometric waveform envelope.

12. A method of estimating bio-information of a user by a foldable electronic device comprising a foldable main body part having a first main body and a second main body, the method comprising:
    obtaining a contact image of an object of the user by a first sensor provided on the first main body when the object is placed into contact with the first main body;
    measuring a degree of folding of the main body part by a second sensor provided on the first main body, the degree of folding being the folding of the first main body relative to the second main body while the object is placed into contact with the first main body; and
    estimating the bio-information of the user, based on a signal obtained from the contact image and the degree of folding,
    wherein the obtaining the contact image comprises obtaining the contact image of the object when the second main body is rotated to press the object against the first main body while the object contacts the first sensor on the first main body, and
    wherein the obtained signal provides bio-information corresponding to one or more of blood pressure, vascular age, arterial stiffness, aortic pressure waveform, vascular compliance, stress index, and fatigue level of the user.

13. The method of claim 12, wherein the measuring the degree of folding comprises measuring the degree of folding of the main body part based on the second main body rotating to press the object while the object contacts the first sensor.

14. The method of claim 12, wherein the estimating the bio-information comprises:
    obtaining a pulse wave signal based on the contact image;
    obtaining contact pressure, exerted by the second main body on the object when the second main body rotates, based on the degree of folding; and
    estimating the bio-information of the user, based on the pulse wave signal and the contact pressure.

15. The method of claim 14, wherein the estimating the bio-information comprises:
    obtaining an oscillometric waveform envelope based on the pulse wave signal and the contact pressure; and
    estimating the bio-information based on the obtained oscillometric waveform envelope.

16. The method of claim 12, further comprising outputting information on a display provided on an outer surface of the second main body for guiding the user to provide contact pressure against the object and first main body having first sensor based on the measured degree of folding.

17. The method of claim 12, further comprising outputting a result of the estimation of the bio-information.

* * * * *